US006352715B1

(12) United States Patent
Hwang et al.

(10) Patent No.: US 6,352,715 B1
(45) Date of Patent: Mar. 5, 2002

(54) TRANSDERMAL RATE-CONTROLLED DELIVERY OF HUPERZINE A FOR TREATMENT OF ALZHEIMER'S DISEASE

(75) Inventors: Kou Mark Hwang, Danville; Suying Liu, Belmont, both of CA (US)

(73) Assignee: Sagittarius Life Science Corp, Taipei Shien (TW)

(*) Notice: Subject to any disclaimer, the term of this patent is extended or adjusted under 35 U.S.C. 154(b) by 0 days.

(21) Appl. No.: 09/591,931

(22) Filed: Jun. 12, 2000

Related U.S. Application Data (63) Continuation-in-part of application No. 09/026,880, filed on Feb. 19, 1998.

(51) Int. Cl.[7] .......................... A61F 13/02; A61F 13/00; A61L 15/16
(52) U.S. Cl. ....................... 424/448; 424/449; 424/443; 424/444
(58) Field of Search .............................. 424/448, 449, 424/443; 514/286

(56) References Cited

U.S. PATENT DOCUMENTS

| 5,177,082 | A | * | 1/1993 | Yu et al. |
| 5,359,087 | A | * | 10/1994 | Johnson et al. |
| 5,663,344 | A | * | 9/1997 | Kozikowski et al. |
| 5,762,953 | A | * | 6/1998 | Venkateshwaren |
| 6,034,117 | A | * | 3/2000 | Hender et al. |

* cited by examiner

Primary Examiner—Thurman K. Page
Assistant Examiner—Isis Ghali
(74) Attorney, Agent, or Firm—Chi Ping Chang; Pacific Law Group LLP (57) ABSTRACT

This invention relates to a novel transdermal drug delivery system whereby Huperzine A ("Hup A"), a naturally occurred Acetylcholine esterase inhibitor traditionally used to alleviate memory problem, is formulated for transdermal administration suitable for the treatment of Alzheimer's Disease ("AD") to increase the efficacy and convenience for outpatient care of AD patients. A controlled-release skin patch designed for once-a-week application of Hup A is provided for easy AD medication according to the invention.

15 Claims, 11 Drawing Sheets

Fig 1: pH-Titration profile of HupA

Fig 2: Solubility-pH Profile of HupA

Fig 3: pH-Partioning profile of HupA

Fig 4: Permeation of Hup-A through human cadaver skin as a function of donor pH

Fig 5: Intrinsic permeability vs donor pH

Fig 6: Amount lost from donor vs pH

Fig 7a: Percent Release of Hup-A from trial patch #1 (Adhesive used ETA-2)

Fig 7b: Percent of Hup-A vs Square root of time from trial patch #1 (Adhesive used ETA-2)

Fig. 8a: Percent Release of Hup-A from trial patch #2 (Adhesive used HY-3)

Fig 8b: Percent of Hup-A released vs Square root of time from trial patch #2 (Adhesive used HY-3)

Fig 9: Permeation of Hup-A through human cadaver skin from trial patch #1 (Adhesive used ETA-2)

Fig 10: Permeation of Hup-A through human cadaver skin from trial patch #2 (Adhesive used HY-3)

Fig 11: Seven days permeation profile for Hup-A using trial patch #2 (Adhesive used HY-3)

TRANSDERMAL RATE-CONTROLLED DELIVERY OF HUPERZINE A FOR TREATMENT OF ALZHEIMER'S DISEASE

RELATED APPLICATION

This application is a continuation-in-part application of a pending application, Ser. No. 09/026,880, filed Feb. 19, 1998.

FIELD OF INVENTION

This invention relates to medicine. In particular, it relates to a novel transdermal drug delivery system and a process for preparing the same whereby a therapeutically effective dose of Huperzine A ("Hup A") can be transdermally administered to patients for the treatment of Alzheimer's Disease ("AD").

BACKGROUND OF THE INVENTION

AD is thought to be the disease of 21 century. It accounts for about 75% of senile dementia. This central nervous system disorder is marked by a variety of symptoms such as degeneration of neurons, development of amyloid plaques, neurofibrillary tangles, declination of acetylcholine and atrophy of cerebral cortex. Patients with AD suffer loss of short-term memory initially and followed by decline in cognitive function and finally loss of the ability to care for themselves.

AD affects about 10% of the population who are beyond age 65. It attacks 19% of individuals 75 to 85 years old, and 45% over age 85. AD is the fourth leading cause of death in adults, behind heart disease, cancer, and stroke. The cost of caring for patients, including diagnosis, nursing, at-home care, and lost wages combined, is estimated to be between $80 billion and $90 billion per year.

Although there are progresses in unfolding pathophysiologic mechanisms of the disease, the cause of AD is still poorly understood. There are several suspected causes such as genetic predisposition (PS-1, PS-2, APP, apoE, CO1, CO2 gene mutations), neurotransmitter defects (Acetylcholine deficiency), inflammation, metabolic decline, free radical stress, or excitatory amino acid toxicity. None of these causes alone is conclusive.

Several compounds are currently under clinical studies for AD according to the current understanding of its pathogenesis. Among these drugs notably are acetylcholine esterase (AchE) inhibitors. Recently, two AchE inhibitors, Tacrine and Donepezil, have received regulatory approval for AD treatment. While Tacrine provides a moderate beneficial effect on deterioration of cognition, it suffers some adverse effects as it causes increases in serum hepatic enzymes. Several other AchE inhibitors with higher potency and better specificity are under clinical investigations. One of these AchE inhibitors is Hup A.

Hup A is an alkaloid isolated from Lycopodium serratum, a Chinese traditional medicinal herb. Hup A appears to be more specific and potent in inhibiting AchE compared to Tacrine and Donepezil as demonstrated in both in vitro and in animal model. The three dimensional crystal structure of the AchE/Hup complex shows a strong hydrophobic interaction between Hup A and the active-site gorge of AchE. Further studies have shown that Hup A is able to permeate through the blood-brain barrier to produce a dose-dependent increase of Ach, norepinephrine, and dopamine in rat cortex by systemic or local administration of Hup A. It appears that Hup A demonstrates promising protective effects to neuron from neurotoxins. Evidences obtained from studies employed rat embryo hippocampus and cerebellum cultured cells have shown that Hup A decreases the death of neuronal cell caused by toxic levels of glutamate. The pharmacokinetics evaluation of a single oral dose of 0.99 mg of Hup A to six volunteers showed that Hup A was absorbed rapidly, distributed widely in the body, and eliminated at a moderate rate. In a small double blind clinical study conducted in China, Hup A administered orally at 0.2 mg (4 tablets, b.i.d) for 8 weeks had demonstrated significant improvement in memory, cognition and behavior in 58% patients without causing any severe side effects to the same.

Administration of drugs for AD patients has to be made convenient for self-medication of the patients as well as for medication rendered by care-givers. Especially in those elderly suffering from memory disorders and dementia, repeated administration of drugs may be difficult as they tend to miss scheduled self-medication or otherwise may require the care-givers to expend extra time ensuring that AD patients are adhered to their medication schedules.

There is therefore an apparent need for drug delivery formulations and a process of making the same which would allow transdermal delivery of Hup A to AD patients at a constant rate for over a period of time after a single Hup A administration such that the patients are assured to receive adequate medication without the need of constant monitoring and supervision.

It is therefore an object of the invention to provide for such novel transdermal drug delivery formulations and process for Hup A through a long-term controlled release skin patch of Hup A for treatment of AD patients.

It is another object of the invention to provide for a method for transdermal Hup A administration through a long-term controlled release skin patch of Hup A to provide therapeutical benefits for AD patients.

It is one more object of the invention to provide a long-term controlled release skin patch of Hup A that will provide therapeutical benefits to AD patients for at least seven (7) days.

These objects are realized by the invention by providing a controlled release skin patch designed for once-a-day or once-a-week application to provide a consistent and systematic method for delivering Hup A to AD patients without constant monitoring and supervision for several days after a single administration.

SUMMARY OF INVENTION

This invention relates to a novel transdermal delivery device for a pharmaceutical composition comprising Hup A which has been proven to reduce and temper the effects of Alzheimer's Disease.

One aspect of the invention is to provide for a transdermal drug delivery device suitable for transdermal administration of Hup A to provide therapeutical benefits to patients with Alzheimer disease. The transdermal drug delivery device comprises (i) a concentration of Hup A in an amount sufficient to enable said Hup A to exhibit anti-Alzheimer activity through said transdermal administration; (ii) at least an aprotic solvent in a concentration sufficient to dissolve said Hup A to from a Hup A reservoir; (iii) a gelling agent in an amount sufficient to gelled said Hup A reservoir; and (iv) at least a polymeric membrane added to encapsulate said gelled Hup A reservoir to form a controlled-release formulation. The Hup A reservoir is adjusted to a pH range in which said Hup A is predominantly in a neutral form to achieve maximum transdermal delivery of said Hup A to provide the therapeutical benefits to the patients. The transdermal drug delivery device according to the invention may be in a form of skin patch with the aid of a drug-impermeable metallic-plastic laminate to said polymeric membrane. Preferably, the pH range of the Hup A reservoir is between 7 to 9.

Another aspect of the invention is to provide for an adhesive-type transdermal drug delivery device suitable for transdermal administration of Hup A to provide therapeutical benefits to patients with Alzheimer disease. Briefly, the adhesive-type transdermal drug delivery device comprises (i) a concentration of Hup A in an amount sufficient to enable said Hup A to exhibit anti-Alzheimer activity through said transdermal administration; (ii) at least a pressure-sensitive adhesive polymer in a concentration sufficient to dissolve said Hup A to from a Hup A adhesive solution in presence of an organic solvent; and (iii) a sheet of drug-impermeable backing laminate added to coat said Hup A adhesive solution to form a pressure-sensitive adhesive formulation. Preferably, the Hup A adhesive solution has a pH value in the range of 7 to 9.

One more aspect of the invention is to provide for a method for preparing the aforementioned transdermal drug delivery device which comprises weighing a concentration of Hup A in an amount sufficient to enable said Hup A to exhibit anti-Alzheimer activity through transdermal administration; dissolving said Hup A in at least an aprotic solvent in a pH range enabling said Hup A existing predominantly in a neutral form to form a Hup A reservoir; adding a gelling agent to gell said Hup A reservoir; and adding at least a polymeric membrane to encapsulate said gelled Hup A reservoir to form a controlled-release formulation.

One further aspect of the invention is to provide for a method for preparing the aforementioned adhesive-type transdermal drug delivery device which comprises weighing a concentration of Hup A in an amount sufficient to enable said Hup A to exhibit anti-Alzheimer activity through transdermal administration; dissolving said Hup A in at least a pressure-sensitive adhesive polymer in presence of a suitable solvent to from a Hup A adhesive solution in a pH range in which said Hup A is predominantly in a neutral form to form a Hup A adhesive solution; and adding a sheet of drug-impermeable backing laminate to coat said Hup A adhesive solution to form a pressure-sensitive adhesive formulation.

Still one further aspect of the invention is to provide for a method for providing therapeutical benefits of Hup A to a human patient diagnosed with Alzheimer disease. The method comprises preparing the aforementioned transdermal drug delivery device and administrating the same to a human patient through dermal administration for a period of time sufficient to exhibit the Alzheimer activities in the human patient.

The foregoing objects and specific construction of the present invention will become apparent and understandable from the following detailed description thereof, when read in conjunction with the accompanying figures.

BRIEF DESCRIPTION OF THE FIGURES

FIG. 7 A and B shows percentage release of Hup-A from trial adhesive ETA-2 patch;

FIG. 8 A and B shows percentage release of Hup-A from trial adhesive HY-3 patch;

DETAILED DESCRIPTION OF THE INVENTION

In order to achieve the preparation of a pharmaceutically acceptable Hup A formulation exhibiting therapeutical activity against AD through transdermal delivery, a series of studies desiring to characterize the physico-chemical properties of Hup A and their effects on permeation profiles of Hup A through human cadaver skin were conducted prior to the development of the transdermal formulations according to the present invention.

EXAMPLE 1

Determination of the Purity of Huperzine A

The purity of the sample of Hup A that was originally obtained from China was verified and confirmed prior to experimentation based on the following procedures and characteristics:

A) Melting point: The melting point of Hup A was determined using a Thomas Hoover Unimelt Capillary Melting Point Apparatus. The melting point was very sharp and was determined to be between 228–229° C., which is substantially close to the literature reported value of 230° C. for Hup A.

B) UV spectroscopy: A solution of Hup A was made in ethanol (0.19061 mM) for UV spectroscopy. The UV absorption spectrum was measured using a UV 160U Spectrophotometer (Shimadzu Scientific Instruments) in the range of 200–400 nm. The absorbance maxima were at 231.6 and 313.2 nm which are similar to literature reported values of 231 and 313 nm. A third maximum was obtained at 205.8 nm which is not reported in literature. Errors in observed are 4.5% and −1.311% for $\lambda_{max}$ 231.6 and 313.2 nm, respectively.

C) Optic rotation: The reported optic rotation of Hup A is $[\alpha]D^{24.5}=-150.4°$ (C=0.498 in MeOH). The optic rotation of the drug in solution was measured using a polarimeter. The measured rotation was −0.727° (+/−0.001), the calculated specific rotation was −146.13° (+/−0.201) and % optical purity=97.16(+/−0.13).

D) HPLC analysis: HPLC analysis was carried out using a C-18 column. All samples were analyzed using HPLC system (Hewlett-Packard model 1050) equipped with an autosampler. The column used was a reversed-phase Hypersil C-18 column (20 cm length and 4.6 mm i.d., 5 um particle size) maintained at 37° C. The mobile phase consisted of 20:80 acetonitrile:water containing 0.02% of triethylamine and 0.05 M phosphoric acid, at a flow rate of 1 ml/min. The sample volume injected for analysis was 25 ul for buffer solution samples and 5 ul for n-octanol samples. The detector used was a variable wavelength UV detector maintained at wavelength of 231 nm. The retention time of Hup A was found to be 6.66 min. A second peak was seen at 4.64 min with peak area corresponding to less 1.65% of the drug peak area. The limit of detection was 0.1 ug/ml and standard curves were prepared over a range of 0.2–150 ug/ml.

The data from the purity studies shows that the relative purity of Hup A used in the present invention is estimated to be 98.35%, 97.16%, 95.5% as measured by HPLC, optic rotation, and molar absorption, respectively.

EXAMPLE 2

Characterization of Physico-chemical Properties of Hup A

A) Determination of pKa of Hup A

A solution of the Hup A was prepared in water to obtain a concentration of $5 \times 10^{-4}$ M solution. Hydrochloric acid solution 0.005M was prepared by dilution of concentrated acid. Similarly, a NaOH solution was prepared by diluting commercially available 1N solution.

For all titration, the procedure used was similar and is described below. The solution to be titrated was taken in a breaker and continually mixed using a magnetic stir bar. A pH electrode was used to measure pH of the solution during the experiments. The pH meter was connected to a computer, which was programmed to automatically obtain pH readings every 10 seconds. The titrant solution was taken in another breaker and a peristaltic pump was used to deliver it as a constant rate. The rate of delivery of the titrant was calibrated and fixed at 0.327 ml/min.

First, the HCL solution was standardized by titrating it with standard NaOH solution. This was carried out three times an d end point was determined from the inflection point using the titration profile. Next, 25 ml of the Hup A solution was taken in the breaker and titrated with the HCL using the same procedure. The initial pH of the solution was around 8.3 and titration was continued till pH fell to about 3. The data obtained gave changes of pH with time. The time axis was then converted to volume of HCL added as rate of addition of HCL was mixed.

The pH titration curve consists of three different regions: initial gradual decrease in pH as the base is slowly neutralized by the acid; middle region showing slow decrease in pH as excess acid is added to the solution. The pKa of the base is calculated from the initial region. The pH corresponding to midpoint of the initial part of the curve is the approximate pKa of the Hup A. Further, the exact pKa of Hup A was calculated by method described by Albert and Sergeant (1971), which is incorporated herein by reference.

Figure 1:
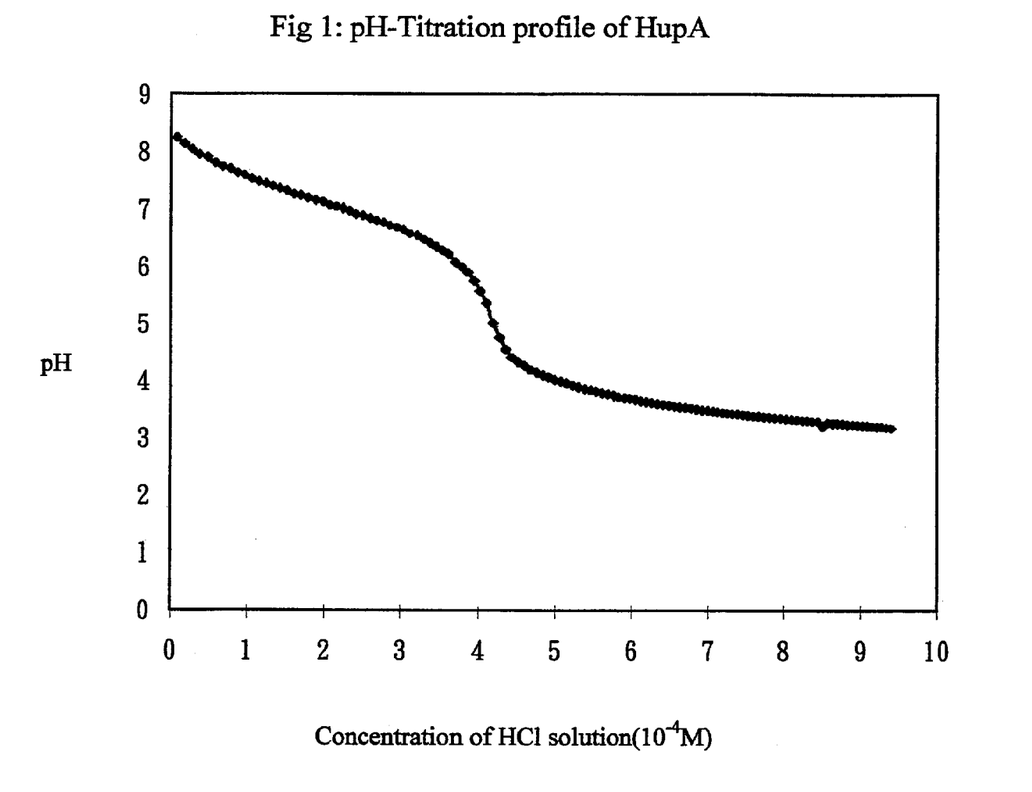
FIG. 1 shows the pH titration profile of the Hup A.

The results of the pH titration profile of the Hup A is shown in FIG. 1. The pKa of Hup A was determined to be 6.97 (+/−0.06). For practical purpose, the pKa value was rounded off to B) Determination of pH/Solubility Profile In order to conserve the drug quantity being used, single point solubility determinations were carried out. Six different buffers were prepared in to determine the solubility of Hup A. The pH range chosen to study solubility is in 2 units above and 2 units below the pKa of the drug, i.e., 5 to 9. In addition, pH 7.4 was also selected to determine solubility at the physiological pH. To determine solubility, weighed amounts of Hup A were added to six different glass vials. In each vial, 1 ml of the respective buffer was added. The vials were tightly closed and kept in a shaking water bath maintained at 37° C. for 24 hours. At the end of such period, the supernatant solution was filtered through 0.22 um nylon filters into pre-warmed tubes. An aliquot of the filtrate was further diluted and analyzed by HPLC.

Figure 2:
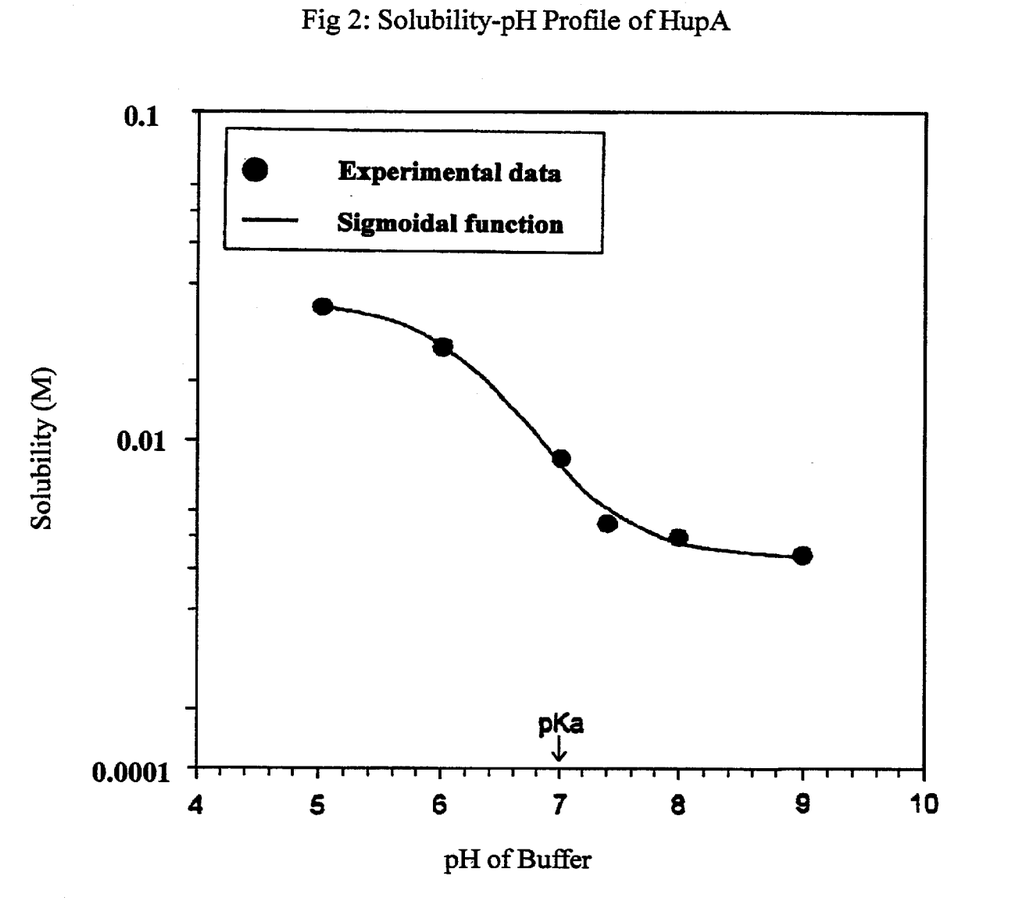
FIG. 2 shows the pH-solubility profile of Hup A.

The results of the pH-solubility profile of Hup A is shown in FIG. 2 and Table 1. It can be seen that at pH 2 units above the pKa, i.e., at pH 9, the solubility of Hup A is the lowest. At low pH, i.e., at pH 5, the solubility of Hup A is seen to be high. This is expected as at pH 5, the drug predominantly exists as an ionized moiety with a single positive charge. These charged ions are hydrophilic and can be easily solubilized by water. At pH 9, the drug predominantly exists as an neutral moiety which is lipophilic, thus the solubility is low. The log of solubility as a function of solution pH is explained by the Henderson-Hasselback equation:

$$pH = pKa + \text{Log}(S_0/S + S_0)$$

wherein S is the total concentration of both ionized and unionized species and $S_0$ is the concentration of undissociated base.

C) Partitioning of Hup A into N-octanol From Buffers of Different pH

The buffers used to prepare solutions of Hup A for the partitioning study were the same as those used in the solubility studies, i.e., isotonic phosphate buffers with pH 5, 6, 7, 7.4, 8 and 9. Initially, 100 ml of n-octanol was mixed with 100 ml of phosphate buffers and placed in shaking water bath at 37° C. for 24 hours to saturate the n-octanol with buffer prior to study. Then the n-octanol was separated from the buffer using a separating funnel.

Solutions of Hup A (about 150 ug/ml concentration) were prepared separately in each of the six buffers. Then 1 ml each of each buffers was pipetted to three test tube. To these test tubes, 1 ml of the n-octanol was added. Controls were set up consisting only of buffer solutions without n-octanol to account for changes in concentration due to evaporation of buffer or degradation of drug if present. The tubes were sealed and placed in a shaking water bath at 37° C. for 48 hrs. Samples of 100 ul each were taken from both the n-octanol layer and the buffer layer and analyzed by HPLC. Partition coefficients were determined from the ratio of concentration of Hup A in n-octanol to that in buffer.

Figure 3:
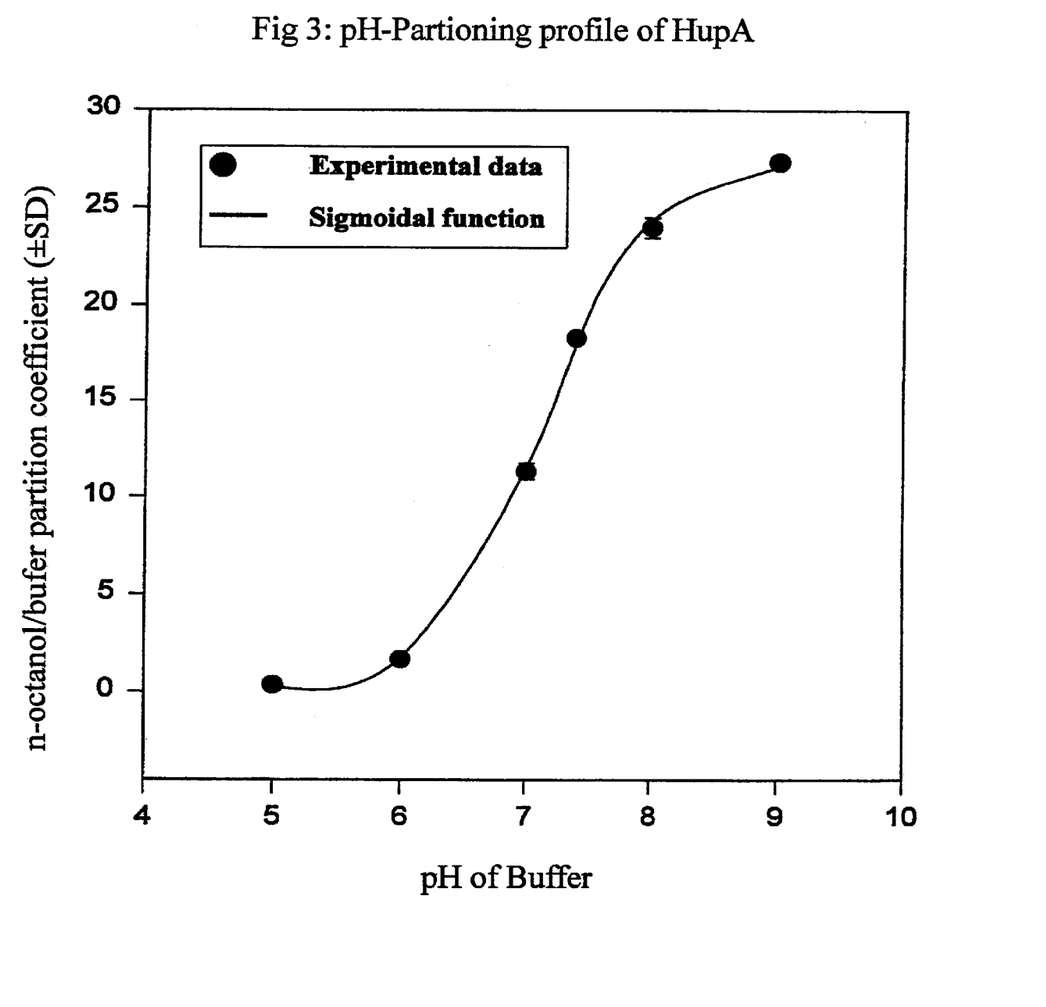
FIG. 3 shows results of the portioning of Hup A into n-octanol from buffers of different pH.

The results of the portioning studies were shown in FIG. 3 and Table 1. It appears that at high pH, when Hup A exists predominantly as a neutral moiety, the partition coefficient is high. As the pH is reduced the fraction of the unionized moiety decreases and so does the partition coefficient. At pH 5, when Hup A exists predominantly as a ionized moiety the partition coefficient is below 1, indicating high affinity of the drug for the buffer phase. The results indicate that the neutral Hup A is more lipophilic than its ionized species.

TABLE 1

Solubility, Partition Coefficient and Permeation Parameters of Hup A

| pH | Solubility (mg/ml +/− SD) | Partition Coefficient (+/− SD) | Permeation arate (ug/cm$^2$/hr +/− SD) | Permeability × 10$^3$ (cm/hr +/− SD) | Intrinsic permeability × 10$^3$ cm$^2$/hr +/− SD) |
|---|---|---|---|---|---|
| 5 | 6.225 (0.153) | 0.352 (0.009) | 0.776 (0.029) | 1.026 (0.038) | 0.0692 (0.001) |
| 6 | 4.639 (0.001) | 1.681 (0.010) | 0.213 (0.088) | 0.290 (0.119) | 0.0146 (0.003) |
| 7 | 2.123 (0.042) | 11.376 (0.415) | 0.633 (0.225) | 0.846 (0.300) | 0.0657 (0.015) |
| 7.4 | 1.325 (0.042) | 18.359 (0.294) | 0.759 (0.368) | 1.007 (0.489) | 0.0741 (0.0310 |
| 8 | 1.201 (0.017) | 24.063 (0.515) | 3.495 (1.3440 | 4.434 (1.7050) | 0.270 (0.017) |
| 9 | 1.044 (0.018) | 27.463 (0.131) | 5.082 (2.162) | 6.118 (2.603) | 0.369 (0.098) |

EXAMPLE 3

Characterization of In Vitro Permeation of Hup A through Human Cadaver Skin

Human cadaver skin is employed as model for studying in vitro transdermal permeation of Hup A. The skin specimens of human cadavers, obtained from Ohio Valley Skin & Tissue Center, are mounted between the two half cells of Valia-Chien Permeation Cell. Donor solutions were prepared in isotonic phosphate buffers of pH 5, 6, 7, 7.4, 8 and 9. Concentration of each solution was about 750 ug/ml. Permeation studies were carried out in triplicate at each pH evaluated. The receptor solution used in each case was isotonic phosphate buffer pH 7.4 to simulate physiological conditions.

As stated above human cadaver skin was used in the permeation studies. The skin, obtained frozen, was first thawed and rinsed with in normal saline. The skin was then blotted to remove excess moisture and cut into 2 cm×2 cm pieces. Each skin piece was sandwiched between two microscope glass slides and the thickness was measured using a micrometer. These skin pieces were then mounted between the two half-cell of Valia-Chien permeation cells, with the stratum corneum facing the donor half-cell. The respective donor and receptor solutions were added (3.3 ml each). Samples of 100 ul each were taken from the receptor compartment at various intervals up to 48 hours and were analyzed by HPLC. The volume of receptor compartment was replaced with fresh isotonic phosphate buffer after each sample. At end of 48 hours, a single aliquot was taken from the donor compartment and analyzed after suitable dilution to evaluate the amount of Hup A lost from the donor in 48 hours.

The rate of Hup A permeation is determined based on the general formula for the determination of the rate of permeation of a drug across a membrane as illustrated by the following equation (1):

$$Jx = Ps(Cd - Cr) \quad (1)$$

Wherein $Jx$ = rate of permeation in ug/cm$^2$/hr $Ps$ = permeability in cm/hr $Cd$ = concentration in donor cell $Cr$ = concentration in receptor cell Sink conditions were maintained throughout the permeation study i.e. Cd>>Cr. Permeability can be calculated using solubility of Hup A as the saturation concentration in donor cell (Cd).

$$Ps = \frac{Jx}{Cd} \quad (2)$$

Intrinsic permeability was calculated by correlating the permeability with the thickness of the skin:

$$P = Ps \times h$$

Wherein P=intrinsic permeability and h=thickness in cm.

Figure 4:
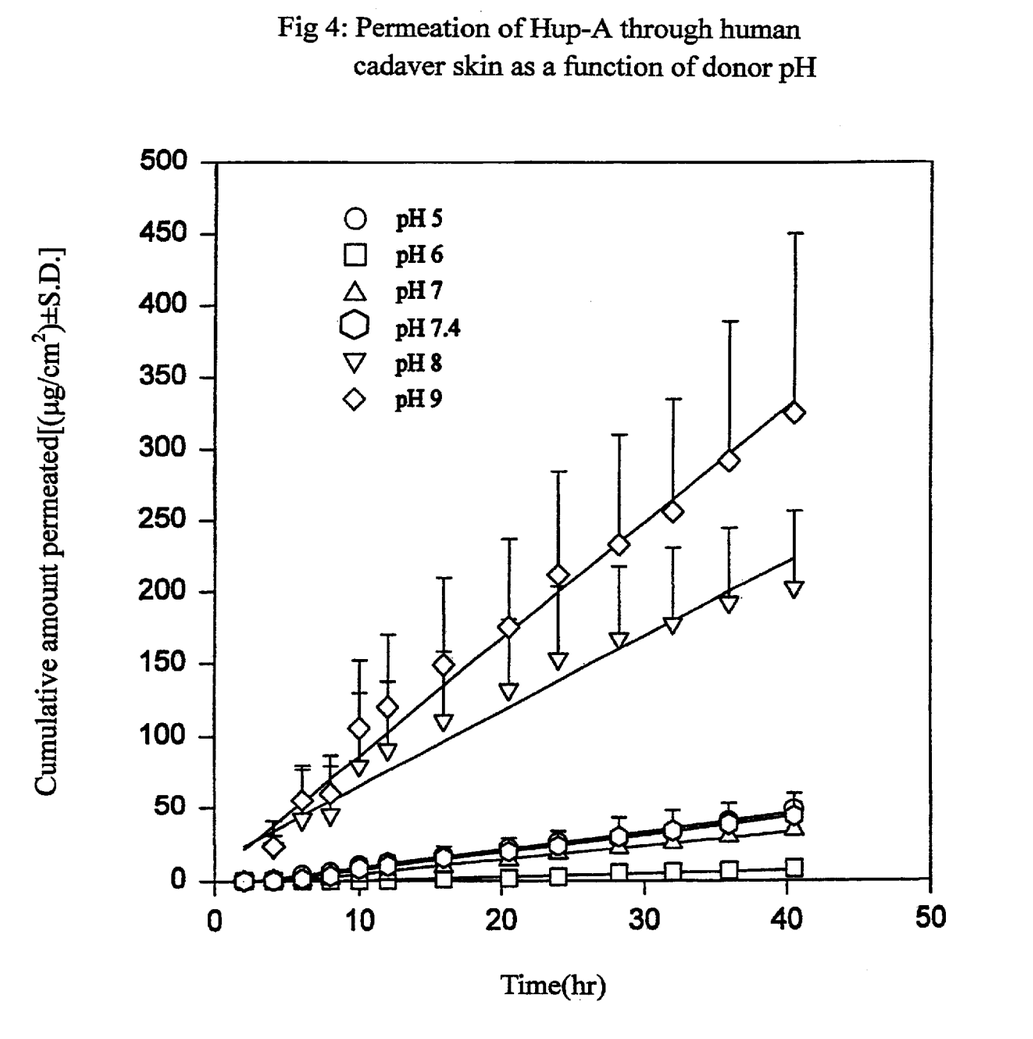
FIG. 4 shows the permeation profiles of Hup A from donors of different pH.
Figure 5:
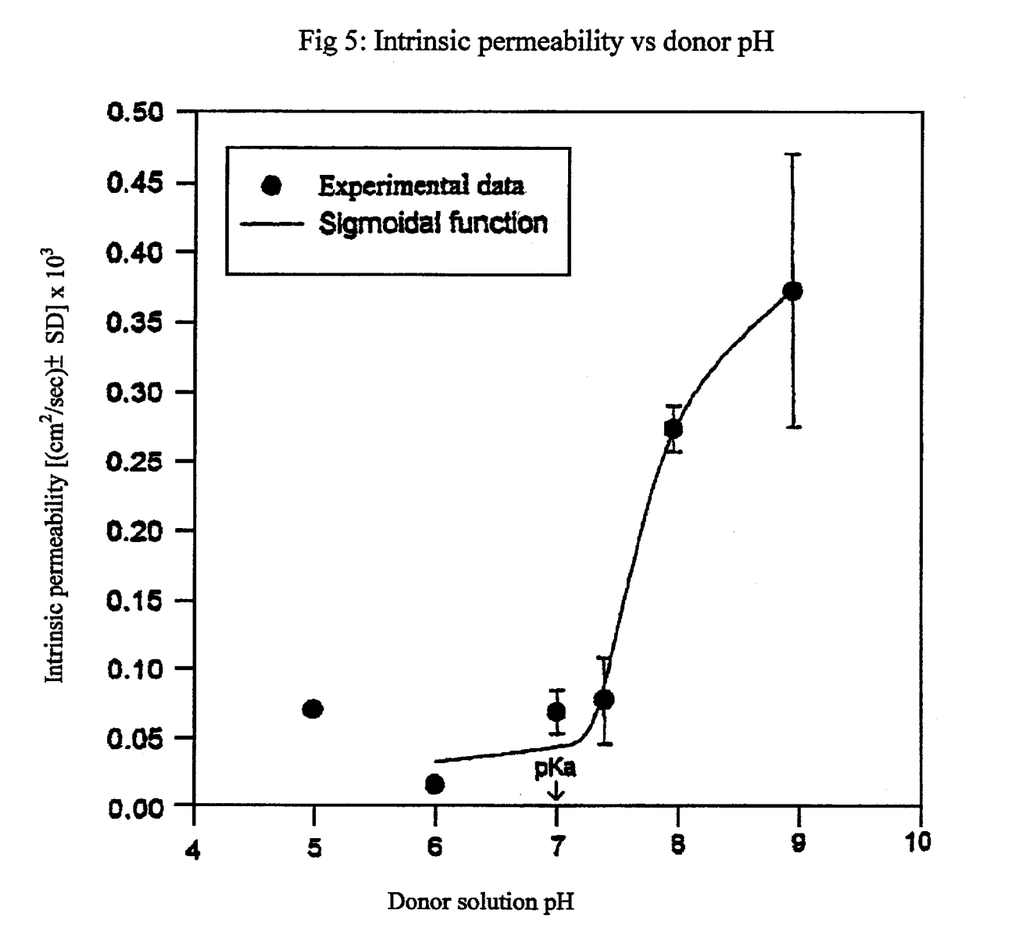
FIG. 5 shows intrinsic permeability-pH profiles of Hup A.
Figure 6:
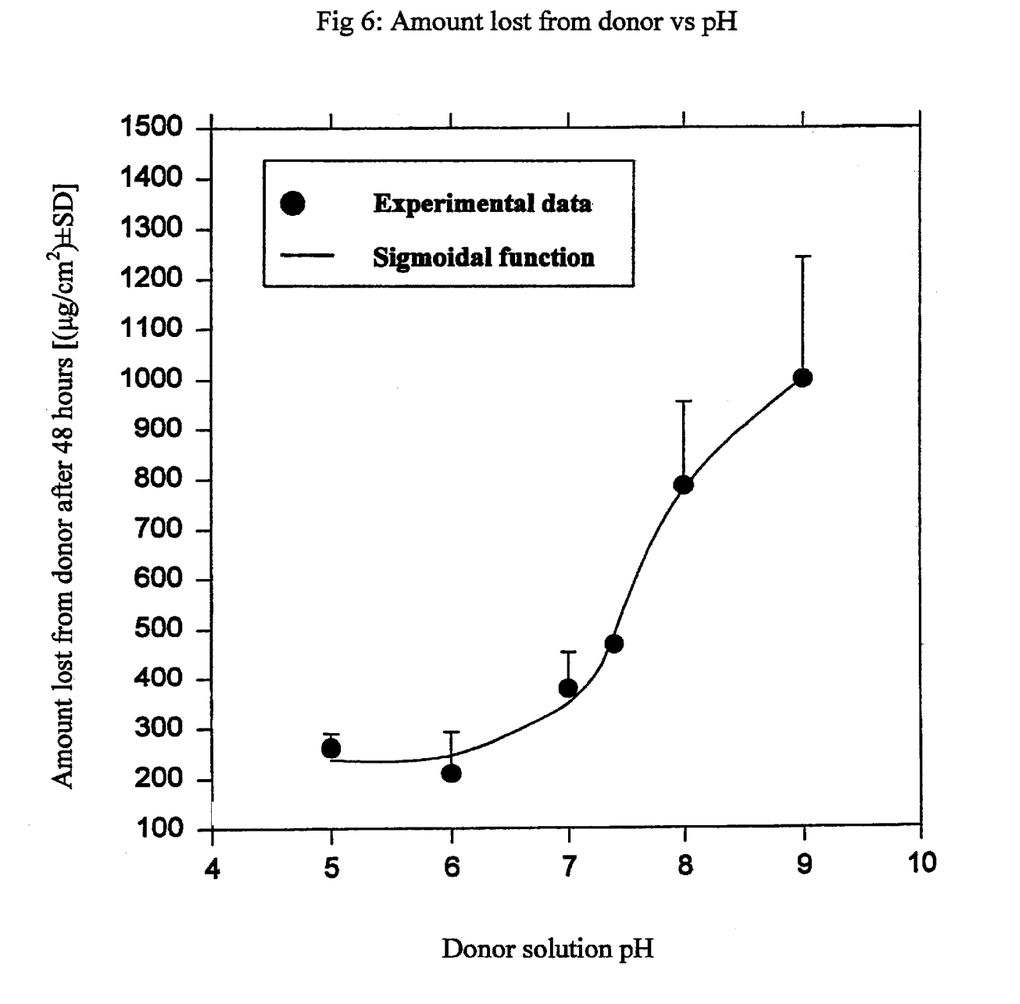
FIG. 6 shows the amount of Hup A lost from donors of different pH.

The permeation profiles of Hup A from donors of different pH are shown in FIG. 4. Generally speaking, higher the partitioning of the drug into the skin, higher the permeation will be. The pH-dependent partitioning behavior of Hup A is seen to be reflected in its skin permeation profiles. The intrinsic permeability-pH profiles of Hup A (FIG. 5) is similar to that observed for partition coefficient-pH relationship (FIG. 3). Again, a sigmoidal relationship is observed. Further, the amount lost from the donor solution, which corresponds to the sum of the amount permeated and the amount retained in the skin, was also seen to follow similar relationship (FIG. 6). The results demonstrated that only the neutral species of Hup A is skin permeable.

The permeation parameters of the Hup A are also summarized in Table 1, which indicates that the intrinsic permeability of neutral Hup A is at least 5 times higher than its protonated species. Thus, to increase total amount permeated with time, a good strategy would be to increase concentration of undissociated form of Hup A in the donor. In addition, this needs to be achieved at pH values closer to physiological pH as extremely acidic or basic formulations can cause skin irritation. A possible method to increase concentration of undissociated form of Hup A may be to add non-polar solvents such as alcohols and glycols. However, these agents also reduce partitioning of drugs into the skin. Thus, various co-solvents need to be evaluated so as to achieve balance of satisfactory solubility and partitioning.

As expected, the pH again plays an important role in permeation behavior of Hup A. A substantially greater permeation of Hup A through the skin was observed at higher pH than that at the lower pH. The intrinsic permeability—pH profile of Hup A is similar to that observed for partition coefficient—pH relationship. The result demonstrated that probably only the neutral species of Hup A is skin permeable. The permeation rate required to achieve the therapeutic levels of Hup A by transdermal delivery is calculated to be 4.2 ug/cm$^2$/hr if a 10 cm$^2$ patch is used. A reservoir formulation or using a combination of co-solvents to increase the skin permeability of neutral Hup A could be a viable approach.

EXAMPLE 4

Development of Formulations For Transdermal Delivery of Hup A

A) Reservoir-Type Transdermal Delivery System (TDS)

A dosage amount of Hup A is dissolved in an aprotic solvent, e.g., ethanol or combination, to form solution-type drug reservoir. This Hup A reservoir is then gelled with gelling agent, e.g., hydroxypropyl cellulose, and encapsuled in a shallow compartment molded from a rate-controlling polymeric membrane and a drug-impermeable metallic-plastic laminate.

The release profile of Hup A from the rate-controlling membrane can be measured using Valia-Chien Skin Permeation dissolution apparatus at 37° C. and the rate of release is measured as a function of the composition of the polymeric membranes for selection of one or more polymeric membranes which control the release of Hup A at constant (zero-order) rate, for 24 hours or longer, with a therapeutically-desirable dosage rate.

The permeation profile of Hup A from the various Hup A/TDSs can be measured using Valia-Chien Skin Permeation Apparatus at 37° C. and the rate of permeation across the human cadaver skin can be studied as a function of the composition of drug reservoir formulation as well as the type of rate-controlling polymeric membranes for selection of one or more TDSs which are capable of delivering Hup A at constant (zero-order) rate, for 24 hours or longer, with a therapeutically-effective dosage rate.

B) Adhesive-Type Transdermal Delivery System

A dosage amount of Hup A is dissolved with a pressure-sensitive adhesive polymer, e.g. polyacrylate, in a combination of organic solvents. The Hup A-adhesive solution is then coated, by solvent-casting technique, onto a flat sheet of drug-impermeable backing laminate. The organic solvents are removed to form adhesive-type TDS, which is cut to size of 10 cm². The release and permeation profiles of Hup A are then evaluated using the same apparatus and procedure outlined above.

Two different pressure sensitive adhesives were chosen for evaluation, ETA-2 and HY-3 obtained from Adhesives research Inc. (Glen Rock, Pa.). Both of these are acrylic adhesives that differ in their chemical properties. ETA-2 is a lipophilic adhesive, consisting predominately of esters with aromatic groups, while HY-3 is a hydrophilic, water absorbing adhesive consisting predominantly of esters with and hydroxyl groups. All other lab chemicals were obtained from Sigma Chemical Co. (St. Louis, Mo.) and used as received. The materials, methods and results of the two adhesives, ETA-2 and HY-3 are discussed below:

(1) METHODS (1.1) Preparation of Adhesive Patches

The amounts of drug and adhesive used in preparation for each formulation are given in Table 2. The amounts were calculated so as to obtain a loading dose of about 1 mg drug per 3.14 cm² patch, with a patch thickness of 75 um. To make the patches, first the required amount of adhesive was weighed out into glass bottles and then the weighed quantity of drug was added to it. The drug and the adhesive were mixed overnight using a rotary mixer. The Hup-A/adhesive suspension or solution (depending on adhesive) was then cast on a backing film using K-bar (Werber Mathis AG, Switzerland). After drying in a fume hood at room temperature for 12 hours to evaporate the solvent from the adhesives, the film was covered with a release liner. Circular patches, of surface area 3.14 cm² (i.e. diameter 2 cm) were cut to obtain the formulated patches. The thickness of the patches was measured using the micrometer screw gauge. The film thickness was obtained by subtracting the thickness of the backing film and release liner from the total thickness of the patch.

TABLE 2

Formulation of Transdermal Patches with two Different Adhesives

| Adhesive | Solid Content Of Adhesive | Drug Added (%) | Setting for Film Casting (uM) | Comments |
|---|---|---|---|---|
| ETA-2 | 30% | 1.5% | 350 uM | Drug did not dissolve in adhesive. A suspension was obtained which Was cast into films. |
| HY-3 | 51% | 2.25% | 200 uM | Drug dissolved to form a uniform Solution which was cast into films. |

(1.2) Evaluation of Patches (1.2.1) Drug Loading (Content)

Three patches of each formulation were used in this study. The release liner from each patch was carefully removed using forceps and the patch was placed in a glass conical flask. Methanol, 25 ml was added to each flask. The flasks were closed tightly and placed in a shaker bath to ensure proper agitation of the mixture. Samples of the supernatant solution were taken after 12, 18 and 24 hours till constant readings were obtained and analyzed by HPLC to calculate the amount of drug in each patch.

(1.2.2.) Drug Rlease Kinetics

Each patch was placed in a glass bottle after removal of the release liner following by adding 25 ml of isotonic phosphate buffer (IPB, pH 7.4) to each bottle. The bottles were placed in a shaking water bath maintained at 37° C. Three patches of each adhesive formulation were evaluated. Samples were taken periodically for 48 hours and analyzed by HPLC methods. At the end of 48 hours the residual drug in each patch was measured by extracting with methanol. The percent drug release kinetics of Hup-A from each patch was then calculated.

(1.2.3.) Drug Permeation Kinetics

Human cadaver skin, obtained from Ohio Valley Skin and Tissue center, was used in the permeation studies. The skin, obtained frozen, was first thawed and rinsed with in normal saline. The skin was then blotted to remove excess moisture and cut into 2 cm×2 cm pieces. Each skin piece was measured by sandwiching the skin between two microscope glass slides and the thickness was measured using a micrometer. Three patches of each adhesive formulation were evaluated. The release liner from each patch was carefully removed using forceps and then the patch was applied on the stratum coneum side of the skin pieces. Firm pressure was applied for a few seconds to ensure proper adhesion of the patches to the skin. These skin pieces were then mounted between the two half-cells of Valia-Chien permeation cells, with the viable epidermis side facing the receptor half-cell. The receptor solution IPB was immediately added to the receptor half-cell. Samples of 100 uL, each were taken from the receptor compartment at various intervals up to 48 hours, were analyzed by HPLC. The volume of the receptor compartment was replaced with fresh isotonic phosphate buffer after each sample.

(1.2.4) Evaluation of Drug Permeation for Extended Periods

Based on the results of the 48-hour drug release studies, the adhesive patches prepared using the HY-3 adhesive were evaluated for up to 8 days to evaluate the feasibility of a once a week patch for Hup-A. Drug permeation studies using human cadaver skin were carried out in the same way as described above, with the exception that the duration of study was 8 days with samples taken every four hours for initial 12 hours and every 12 hours thereafter. Care was taken to ensure that the concentration in the receptor compartment remained low so as to maintain sink conditions.

(1.2.5) Analytical Method

All samples were analyzed using a HPLC system (Hewlett-Packard model 1050) equipped with an autosampler. The column used was a reversed phase Hypersil C-18 column (20 cm length and 4.6 mm i.d., 5 um particle size) maintained at 37° C. The mobile phase consisted of 20:80 acetonitrile: water containing 0.02% of triethylamine and 0.05M phosphoric acid, at a flow rate of 1 ml/min. The sample volume injected for analysis was 25 ul for buffer solution samples and 5 ul for n-octanol samples. The detector used was a variable wavelength UV detector maintained at wavelength of 231 nm. The limit of detection was 0.1 ug/ml and standard curves were prepared over a range of 0.1–125 ug/ml.

(2) RESULTS AND DISCUSSION (2.1) Characterization of Adhesive Patches (2.1.1) Drug Content The patches of Hup-A dispersed in both adhesives were found to have comparable thickness, i.e. ETA-2 adhesive were found to be of 75 um thickness, while those of HY-3 were found to be of 80 um thickness. The drug content in each 3.14 $cm^2$ patch was 1.086 (0.022) mg for the ETA-2 patches while for the HY-3 patches, it was 1.062 (0.029) mg. Thus it is seen that the patches prepared from the two adhesives were comparable in both their thickness and drug content. So any differences seen in further drug release and permeation studies would be an effect of intrinsic interaction between the adhesive and the drug and not simple due to formulation factors.

(2.1.2) Release Profiles

Figure 7A:
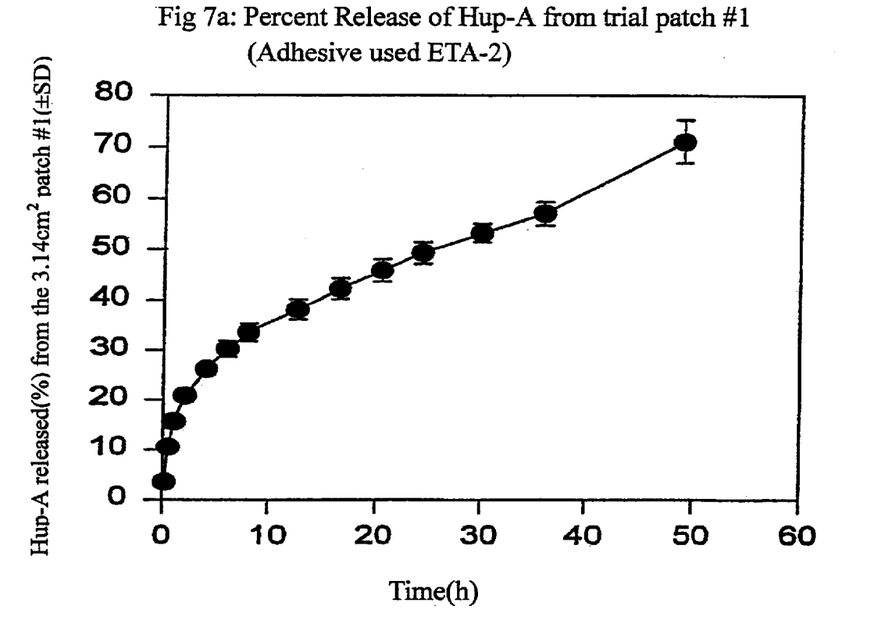
Figure 7B:
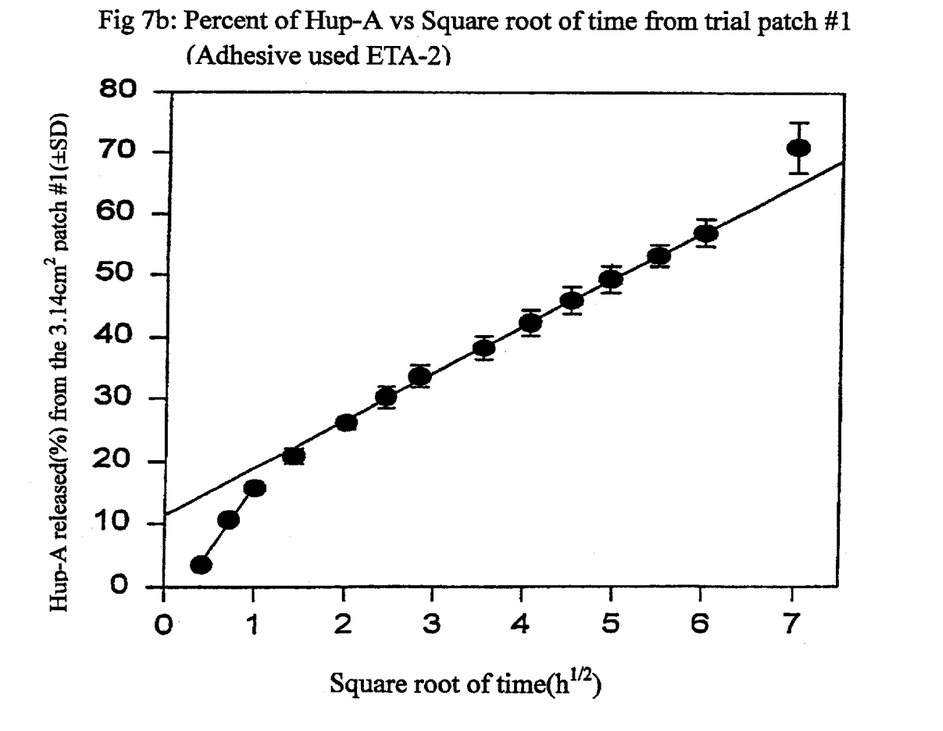

The 48-hour release profile of Hup-A from ETA-2 is shown in FIG. 7A while the square root of time release profile is seen in FIG. 7B. It was observed from the release profile that there appears to be an initial burst phase for about 1-hour, i.e. phase when there is a very rapid release of the drug from the adhesive. As mentioned earlier, the Hup-A did not dissolve in this adhesive, instead it formed a suspension. When the patches are cast from this suspension, the drug is still present as crystals dispersed in the adhesive matrix. The initial burst phase may due to rapid dissolution of the crystals of drug on the surface of the adhesive patch. Once these are depleted, a linear square root of time profile is seen which is characteristic of a matrix diffusion system. Also, it is seen that even after 48 hours of release study, only 70% of the drug are released indicating a strong interaction between the adhesive and drug.

Figure 8A:
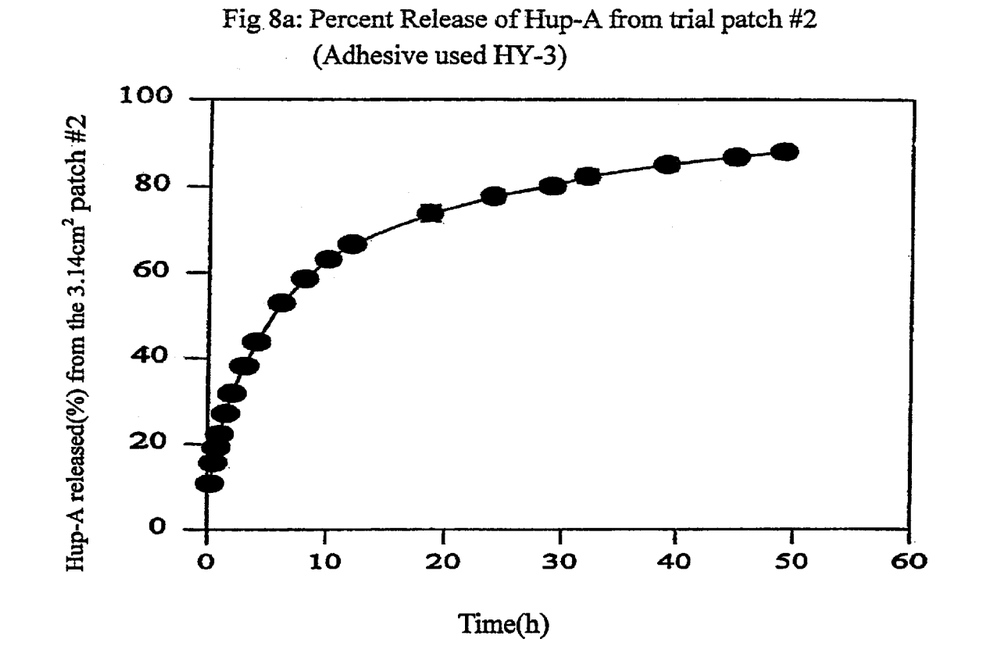
Figure 8B:
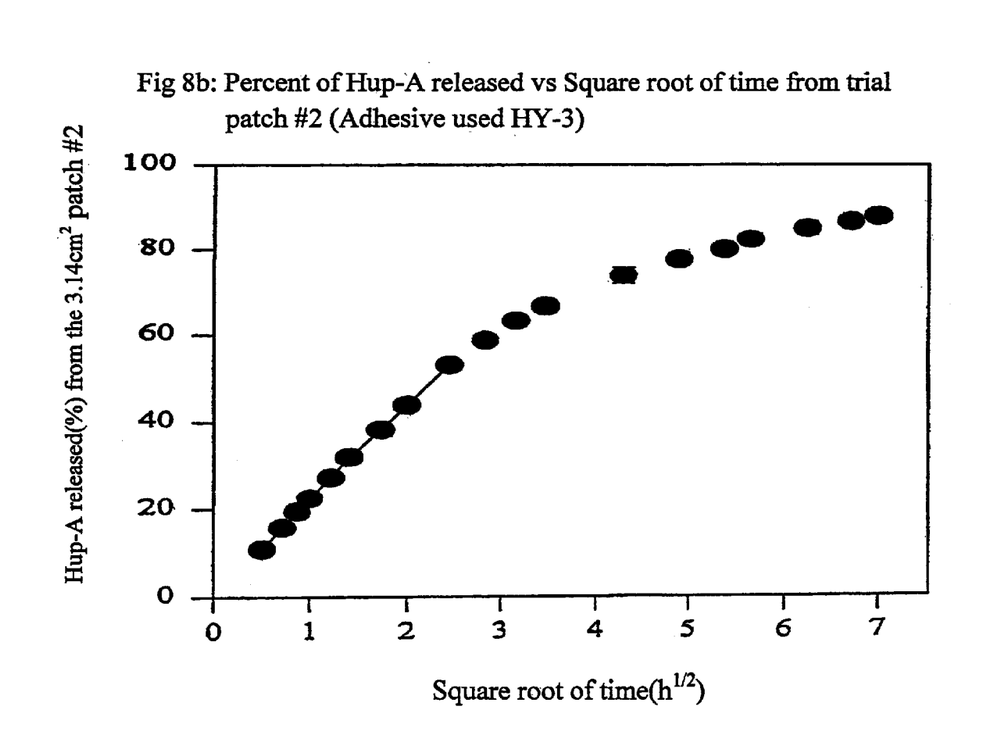

The release profile of Hup-A from the HY-3 adhesive is shown in FIG. 8A while its square root of time profile is shown in FIG. 8B. An important difference seen in these profiles from the ETA-2 adhesive profiles is the absence of a burst phase. The square root of time profile is seen to be biphasic. The initial linear portion lasts for about 8–10 hours during which 65% of the drug is released, which is then followed by a slower release rate. An explanation for this slower release profile is the depletion of drug from the layers closer to the surface. As the drug from the lower layers has to diffuse out, it has to traverse over a longer distance to be released from the patch leading to the plateauing of the drug release profile. At 48 hours, about 90% of the drug content were found to be released. This thus indicates lower interaction of the drug with the adhesive.

From the drug release profiles it thus appears that the adhesive HY-3 demonstrates a better control over the release of Hup-A as compared to ETA-2. It also has a lesser affinity for the drug and may be better suited to the development of an adhesive dispersion type of TDDS for transdermal Hup-A application.

(2.1.3) Two Day Permeation

Figure 9:
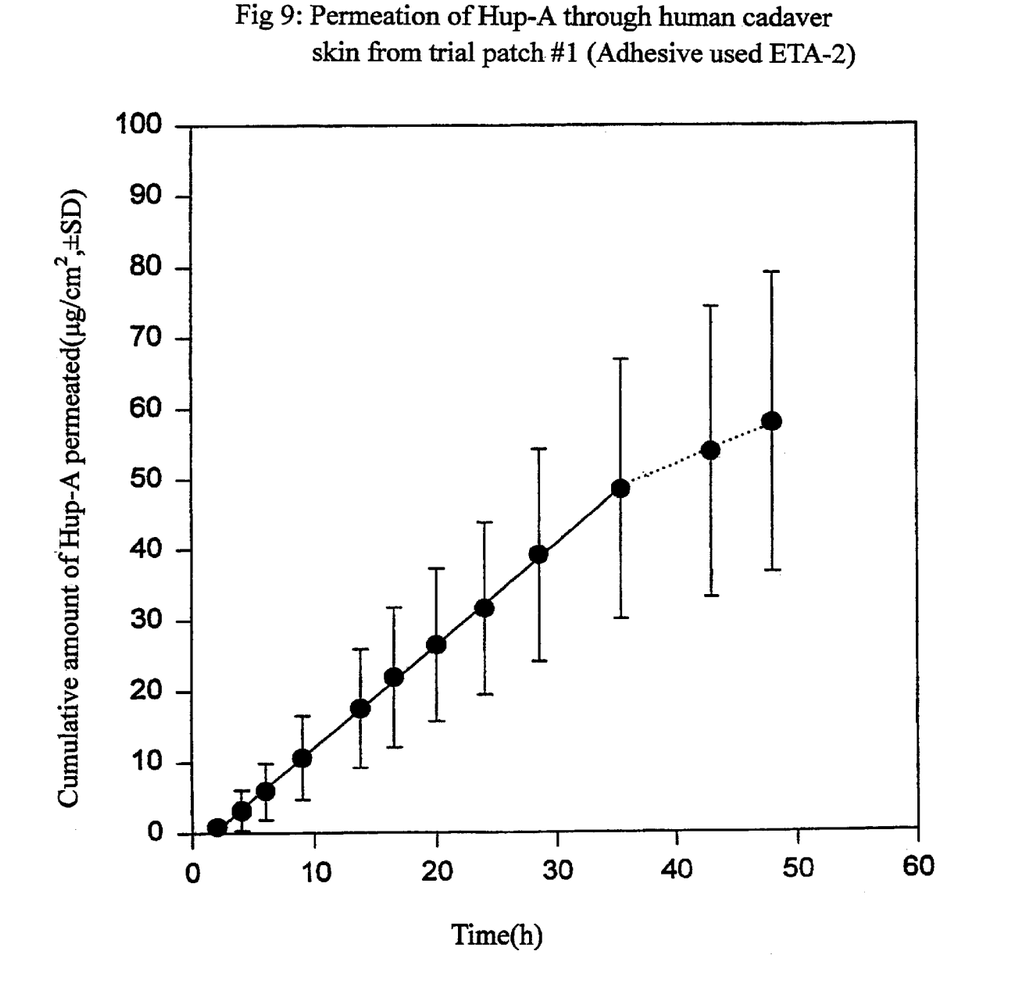
FIG. 9 shows the permeation profile of Hup-A through human cadaver skin from the trial adhesive ETA-2 patch.

The permeation profile of Hup-A from the ETA-2 adhesive is shown in FIG. 9. It was seen that a linear permeation profile was obtained for about 36 hours without presence of any lag-time. After 36 hours the permeation of Hup-A was seen to occur at a much lower rate. During the initial 36 hours, the amount of drug permeated is about 50 $ug/cm^2$, which corresponds to 15% of drug content per $cm^2$ in the patch. As previously discussed, the initial burst phase of Hup-A accounts for this release, which is followed by a slower rate of release. It is thus seen that after the initial 15% of the drug released are depleted, the rate of permeation of drug slows down giving rise to the biphasic drug permeation profile. This type of profile is undesirable for the development of TDDS as it would not be expected to show a constant drug delivery rate.

Figure 10:
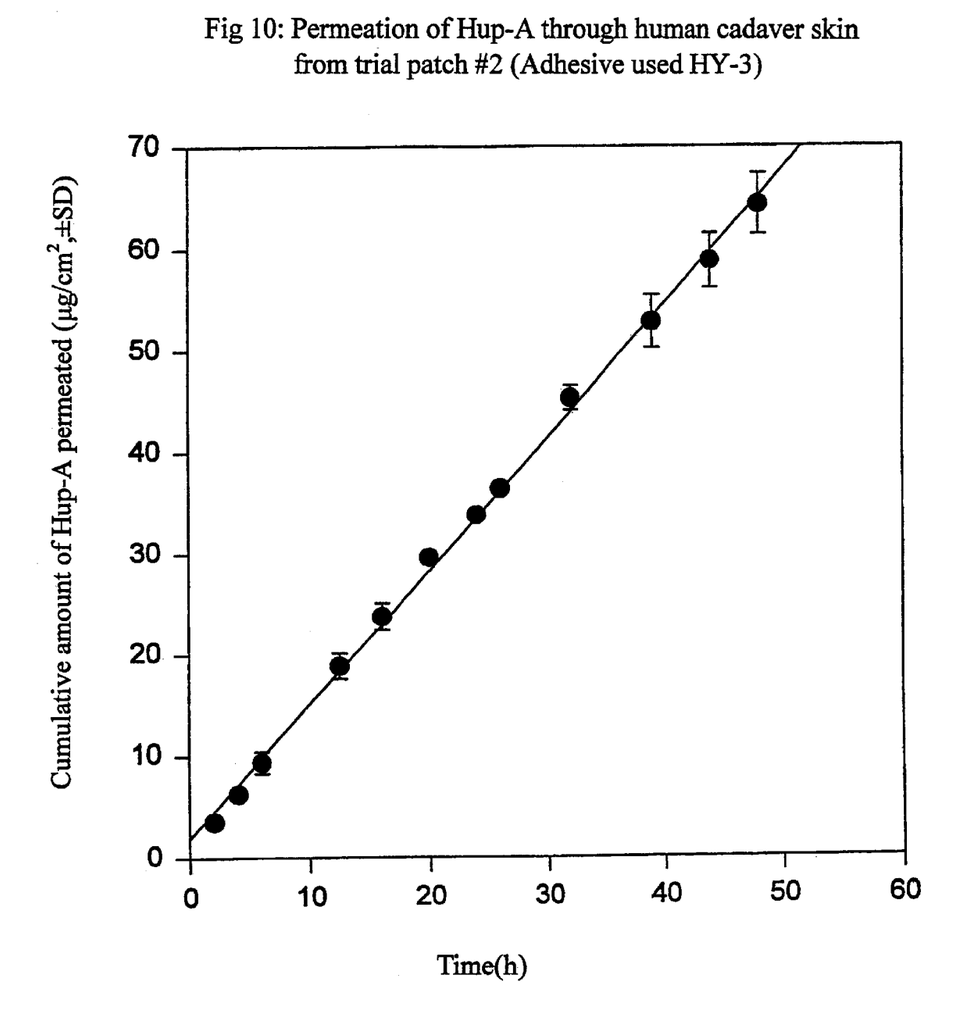
FIG. 10 shows the permeation profile of Hup-A through human cadaver skin from the trial adhesive HY-3 patch.

The drug permeation profile from the HY-3 adhesive system on the other hand demonstrated an excellent linearity over the 48-hour period of study (FIG. 10). The permeation rate obtained 1.32 $ug/cm^2.h$ was above the estimated required rate of 0.833 $ug/cm^2.h$ Hup-A delivery. Thus the HY-3 adhesive system seems to be well suited for the development of a TDDS for Hup-A delivery. Furthermore, the total amount of drug permeated in 48 hours was 64.41 $ug/cm^2$ that is only 19% of the total drug content per $cm^2$ (388.43 $ug/cm^2$). Considering the high cost of the drug, it might be of greater benefit to develop a TDDS capable of delivering Hup-A for longer period of time. With this objective in mind, permeation studies were carried out over 8 days to evaluate feasibility of this system for once-per-week application.

(2.1.4) 7-Day Permeation

Figure 11:
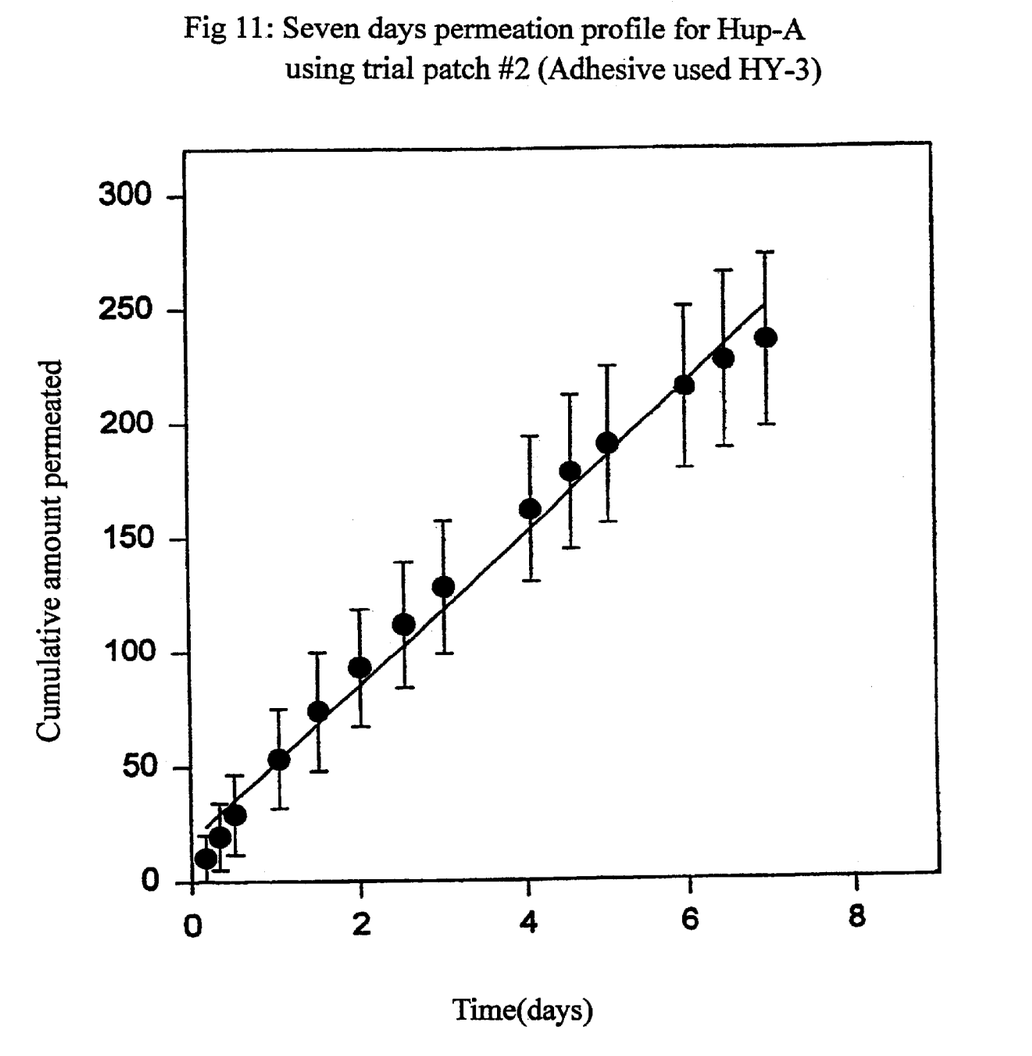
FIG. 11 shows the seven-day permeation profile of Hup-A through human cadaver skin from the trial adhesive HY-3 patch.

The 7-day permeation profile of Hup-A from the HY-3 adhesive system is shown in FIG. 11. It was observed that there is no sudden change in the rate of permeation over the 7-day period that would suggest change in mechanism of release. Although the calculated linearity of the profile was (r2=0.98) was good, a slight curvature is evident. This indicates a gradual reduction in rate of transdermal permeation. The most likely reason for this may be the depletion of the drug from the layers of adhesive adjacent to the skin. As the drug from the layers further away has to diffuse through a longer distance before reaching the skin, the rate of permeation is also reduced. Another reason may be the increase in concentration of the receptor compartment which leading reduction in the concentration gradient across the skin. This factor would not come into play under the in-vivo situation, where the drug diffusing across the skin would be rapidly cleared away by the microcirculation, thus always maintaining the concentration gradient. A summary of all drug release parameters and permeation parameters is shown in Table 3. From the results obtained to date we believe that a once-a-week transdermal drug delivery system for Hup-A is demonstrated.

TABLE 3

Summary of Drug Release and Permeation Parameters

| Adhesive Parameters* | ETA-2 | HY-3 | |
|---|---|---|---|
| Drug Content | | | |
| mg/3.14 cm$^2$ | 1.086 (0.22) | 1.062 (0.295) | |
| Thickness | 75 uM | 80 uM | |
| Drug Release Profiles | | | |
| Initial Rate (% released/h$^{1/2}$) | 20.491 (0.755) | 21.472 (0.608) | |
| Time for Initial Release | 1 hr | 8 hr | |
| Final Rate (% released/$^{1/2}$) | 8.347 (0.398) | 5.865 (0.159) | |
| Percent Released in 48 h | 71.00 (4.20) | 87.99 (1.15) | |
| Permeation Rate | | 48 Hours | 7-days |
| (ug/cm$^2 \cdot$ h) | 1.450 (0.48) | 1.341 (0.06) | 1.386 (0.15) |

*Numbers in parenthesis indicate +/− standard deviation.

(3) SUMMARY AND CONCLUSIONS

Two different adhesives were evaluated for their potential use as adhesive matrices for development of TDDS for Hup-A. It was observed that Hup-A did not dissolve in the lipophilic adhesive ETA-2. Drug release profile of Hup-A from this adhesive demonstrated a burst phase followed by a slower square root of time profile. The transdermal permeation profile was found to be linear for only 36 hours, thus indicating that this adhesive was not suitable for development of TDDS for Hup-A.

On the other hand, the hydrophilic adhesive HY-3 was found to be more suitable. The drug release was found to follow a linear square root of time profile till over 60% of drug were released, followed by a slower phase. The transdermal permeation profile was found to show linearity for up to at least 7 days. This adhesive thus merits the development of a TDDS for Hup-A for once-a-week application.

The drug release rate obtained over 7 days was 1.39 (+−0.15) ug/cm$^2$.h, which is higher than the estimated required rate of 0.833 ug/cm$^2$.h using a 10 cm$^2$ patch. Thus the feasibility of development of a 7-day patch employing a hydrophilic adhesive including, but not limited to, HY-3 for Hup-A appears to be very promising.

Although the preferred embodiment of the invention has been disclosed for illustrative purposes, those skilled in the art will appreciate that various modifications, additions and substitutions are possible, without departing from the scope and spirit of the invention, as disclosed in the accompanying claims

What is claimed is:

1. A rate-controlled transdermal drug delivery device for transdermal delivery of Huperzine A at a therapeutically effective rate in a linear square root of time manner for up to at least 7 days to provide therapeutical benefits to patients with Alzheimer's disease, comprising;
   (a) a concentration of Huperzine A in an amount sufficient to enable transdermal delivery of said Huperzine A at said therapeutically effective rate of no less than 0.833–1.46 ug/cm$^2$.h to exhibit said therapeutical benefits;
   (b) a solution of adhesive polymer in a concentration sufficient to form a Huperzine A dispersing pressure-sensitive adhesive with said concentration of Huperzine A wherein said solution of adhesive polymer is adjusted to a pH range in which said concentration of Huperzine A is predominantly in a neutral form to achieve transdermal delivery of said Huperzine A at said therapeutically effective rate in said linear square root of time manner for up to at least 7 days per one administration; and
   (c) a sheet of drug-impermeable backing laminate added to support said Huperzine A dispersing pressure-sensitive.

2. The transdermal drug delivery device of claim 1 wherein said solution of adhesive polymer is polyacrylate.

3. The transdermal drug delivery device of claim 1 wherein said Huperzine A dispersing pressure-sensitive adhesive is a lipophilic, water absorbing adhesive.

4. The transdermal drug delivery device of claim 3 wherein said lipophilic adhesive is selected from the group consisting of esters with hydroxyl groups.

5. The transdermal drug delivery device of claim 1 wherein said range of pH is between 7 and 9.

6. A method of preparing a rate-controlled adhesive transdermal drug delivery device suitable for transdermal delivery of Huperzine A at a therapeutically effective rate in a linear square root of time manner for up to at least 7 days to provide therapeutic benefits to patients with Alzheimer's disease, comprising the steps of:
   (a) weighing a concentration of Huperzine A in an amount sufficient to enable transdermal delivery of said Huperzine A at the therapeutically effective rate of no less than 0.833–1.46 ug/cm$^2$.h to exhibit said therapeutical benefits;
   (b) dissolving said Huperzine A in a solution of adhesive polymer in presence of a suitable solvent to from a Huperzine A dispersing pressure-sensitive adhesive wherein said solution of adhesive polymer is in a pH range in which said Huperzine A is predominantly in a neutral form to achieve said rate-controlled transdermal delivery of Huperzine A at the therapeutically effective rate in said linear square root of time manner for up to at least 7 days per one administration; and
   (c) adding a sheet of drug-impermeable backing laminate to support said Huperzine A dispersing pressure-sensitive adhesive.

7. The method of preparing an adhesive transdermal drug delivery device of claim 6 wherein said solution of adhesive polymer is polyacrylate.

8. The method of preparing an adhesive transdermal drug delivery device of claim 6 wherein said Huperzine A dispersing pressure-sensitive adhesive is a lipophilic, water absorbing adhesive.

9. The method of preparing an adhesive transdermal drug delivery device of claim 8 wherein said lipophilic, water absorbing adhesive is selected from the group consisting of esters with hydroxyl groups.

10. The method of preparing an adhesive transdermal drug delivery of claim 6 wherein said range of pH is between 7 and 9.

11. A method of providing therapeutical benefits of Huperzine A to a human patient diagnosed with Alzheimer's disease, comprising:
  (a) preparing a transdermal drug delivery device suitable for transdermal administration of said Huperzine A to said human patient, said transdermal drug delivery device comprising:
    (i) a concentration of Huperzine A in an amount sufficient to enable transdermal delivery of said Huperzine A at a therapeutically effective rate at or higher than 0.833–1.46 ug/cm$^2$.h in a linear square root of time manner for up to at least 7 days;
    (ii) a solution of adhesive polymer in a concentration sufficient to dissolve said concentration of Huperzine A to form a Huperzine A dispersing pressure-sensitive adhesive wherein said concentration of Huperzine A is adjusted to a pH range in which said Huperzine A is predominantly in a neutral form to achieve transdermal delivery of said Huperzine A at said therapeutically effective rate for up to at least 7 days;
    (iii) a sheet of drug-impermeable backing laminate added to support said concentration of Huperzine A to form the dispersing pressure-sensitive; and
  (b) administrating said human patient with said transdermal drug delivery device to provide said therapeutic benefits.

12. The method of preparing an adhesive transdermal drug delivery device of claim 11 wherein said solution of adhesive polymer is polyacrylate.

13. The method of preparing an adhesive transdermal drug delivery device of claim 4 wherein said Huperzine A dispersing pressure-sensitive adhesive is a lipophilic, water absorbing adhesive.

14. The method of preparing an adhesive transdermal drug delivery device of claim 13 wherein said lipophilic, water absorbing adhesive is selected from the group consisting of esters with hydroxyl groups.

15. The method of preparing an adhesive transdermal drug delivery device of claim 11 wherein said range of pH is between 7 and 9.

* * * * *